(12) United States Patent
Kim et al.

(10) Patent No.: US 10,295,468 B2
(45) Date of Patent: May 21, 2019

(54) FLUORESCENT IMAGE SYSTEM

(71) Applicant: NATIONAL CANCER CENTER, Goyang-si, Gyeonggi-do (KR)

(72) Inventors: Seok Ki Kim, Seoul (KR); Sung Chun Kim, Goyang-si (KR); Sun Up Park, Seoul (KR)

(73) Assignee: NATIONAL CANCER CENTER, Goyang-si (KR)

( * ) Notice: Subject to any disclaimer, the term of this patent is extended or adjusted under 35 U.S.C. 154(b) by 3 days.

(21) Appl. No.: 15/553,858

(22) PCT Filed: Jan. 29, 2016

(86) PCT No.: PCT/KR2016/000966
§ 371 (c)(1),
(2) Date: Aug. 25, 2017

(87) PCT Pub. No.: WO2016/137129
PCT Pub. Date: Sep. 1, 2016

(65) Prior Publication Data
US 2018/0052107 A1 Feb. 22, 2018

(30) Foreign Application Priority Data
Feb. 26, 2015 (KR) ........................ 10-2015-0027418

(51) Int. Cl.
*G01N 21/64* (2006.01)
*G01N 21/17* (2006.01)
(Continued)

(52) U.S. Cl.
CPC ........... *G01N 21/6456* (2013.01); *A61B 1/04* (2013.01); *A61B 1/06* (2013.01); *A61B 5/00* (2013.01);
(Continued)

(58) Field of Classification Search
CPC ....... G01N 21/6456; G01N 2021/6471; G01N 2021/1736; G01N 21/17;
(Continued)

(56) References Cited

U.S. PATENT DOCUMENTS 6,122,042 A * 9/2000 Wunderman ............ A61B 1/05
356/343
6,915,154 B1 * 7/2005 Docherty ............. A61B 5/0275
600/431
(Continued)

FOREIGN PATENT DOCUMENTS

JP 2005-065976 A 3/2005
KR 10-2011-0088676 A 8/2011
(Continued)

OTHER PUBLICATIONS

International Search Report (in English and Korean) and Written Opinion (in Korean) of the International Searching Authority issued in PCT/KR2016/000966, dated May 25, 2016, ISA/KR.

*Primary Examiner* — Seung C Sohn
(74) *Attorney, Agent, or Firm* — Harness, Dickey & Pierce, P.L.C.

(57) ABSTRACT

The present invention relates to a fluorescent image system capable of generating white light by mixing three monochromatic lights, i.e. red, green and blue monochromatic lights, having a narrow band wavelength, instead of white light of constant wavelength; providing a fluorescent image-use light source that generates a mixed light by adding a fluorescent excitation light source suitable for fluorescent substances; and photographing a general image and fluorescent image simultaneously with the light sources. The fluorescent image system includes a monochromatic light source to generate white light by mixing red, green and blue monochromatic lights, and a fluorescent excitation light source for fluorescent images; and includes a mixed light
(Continued)

source to provide a mixed light which mixes monochromatic light and fluorescent light, and an image photographing device which separates the wavelengths of visible light and fluorescent light in the mixed light, and photographs a general image, fluorescent image and mixed image.

7 Claims, 9 Drawing Sheets

(51) Int. Cl.
    *A61B 1/06* (2006.01)
    *G06T 7/90* (2017.01)
    *A61B 1/04* (2006.01)
    *A61B 5/00* (2006.01)
    *G01J 3/10* (2006.01)
    *G01J 3/44* (2006.01)

(52) U.S. Cl.
    CPC .......... *A61B 5/0071* (2013.01); *A61B 5/0084* (2013.01); *G01J 3/10* (2013.01); *G01N 21/17* (2013.01); *G06T 7/90* (2017.01); *G01J 3/4406* (2013.01); *G01J 2003/104* (2013.01); *G01J 2003/106* (2013.01); *G01N 2021/174* (2013.01); *G01N 2021/1736* (2013.01); *G01N 2021/6417* (2013.01); *G01N 2021/6471* (2013.01); *G06T 2207/10064* (2013.01)

(58) Field of Classification Search
    CPC ...... G01N 2021/6417; G01N 2021/174; G01J 3/10; G01J 2003/106; G01J 2003/104; G01J 3/4406; A61B 5/0084; A61B 5/0071; A61B 5/00; A61B 1/06; A61B 1/04; G06T 2207/10064; G06T 7/90
    USPC ........................................................ 250/226
    See application file for complete search history.

(56) References Cited

U.S. PATENT DOCUMENTS

| 7,722,534 B2 | 5/2010 | Cline et al. |
| 8,046,055 B2 | 10/2011 | Miwa et al. |
| 2011/0270092 A1 | 11/2011 | Kang et al. |
| 2013/0309169 A1 | 11/2013 | Kim et al. |
| 2015/0018690 A1 | 1/2015 | Kang et al. |

FOREIGN PATENT DOCUMENTS

| KR | 10-2012-0015849 A | 2/2012 |
| KR | 10-1173325 B1 | 8/2012 |
| KR | 10-2015-0007679 A | 1/2015 |

\* cited by examiner

FLUORESCENT IMAGE SYSTEM

CROSS-REFERENCE TO RELATED APPLICATION

The present application is the US national phase of International Patent Application No. PCT/KR2016/000966, filed Jan. 29, 2016, which claims priority to Korean Patent Application No. 10-2015-0027418, filed on Feb. 26, 2015. The disclosures of the above-listed applications are hereby incorporated by reference herein in their entirety.

TECHNICAL FIELD

The invention relates a fluorescent imaging system capable of imaging a normal light image and fluorescent image at the same time. Simultaneous imaging of both is made possible by illuminating the scene with a light mixed with a fluorescence excitation light and a white light composed of three narrow-band monochromatic lights which are red, green and blue.

BACKGROUND

In general, an imaging device including an endoscope or a laparoscope includes a light source, a lens and a sensor (camera) for acquiring the light reflected from the object. In an endoscope, laparoscope or other imaging systems, imaging device takes the reflected light from the object where the light source is usually a white light. The use of a fluorescent imaging system is increasing as it helps diagnose specific diseases by imaging the fluorescent emission from the object illuminated by an excitation light having a particular wavelength.

The fluorescent material can be present within a living body or may be injected from outside the body. Fluorescence due to the intrinsic fluorescent material is called autofluorescence. Autofluorescence changes by the biological condition or disease. Measuring the change of it can help diagnose the disease. Injected fluorescent material can also be helpful as the distribution of fluorescence changes by the biological condition.

In the imaging device such as an endoscope, laparoscope or fluorescence, a normal light image which is a reflection of white light is the primary image, and fluorescent image serves only as a supplementary. Thus, the natural reflected image is more frequently used, and seldom required only the fluorescent image. It is advantageous to include a normal light image even in the fluorescent imagery. For example, when the resection of the tumor is performed using a fluorescence imaging system, it is safer to see both the normal light image and the fluorescent image as that may reveal particular conditions of the surrounding normal tissues and vessels.

A conventional imaging method to obtain a normal light image, a reflected image, and a fluorescent image uses mirrors to change the sources and light path mechanically, or beam splitters to separately obtain each image, along with multiple light sources and multi-mode cameras. The method using mirrors is described in the U.S. Pat. No. 7,722,534.

Such methods have disadvantages like low durability and may show early mechanical failure due to the complex structure, and only a limited amount of light received as the images are acquired in a time-sharing manner. Using a beam splitter also suffers from a reduced amount of input light as it divides and distributes light for multiple targets. The previous method for obtaining a normal light image and fluorescent image together cannot help but to rely on such complicated methods as the wavelength of the emitted fluorescent light lies inside the spectrum of the white light which is continuous over the spectrum range. As far as the illumination source is a white light having continuous spectrum, simultaneous acquisition of the normal light image and the fluorescent image is impossible.

The reason is that the wavelength of the white light source ranges between 350~750 nm and sometimes expands further over 750 nm including infra-red-light range. The emitted fluorescent light mixes with the reflected white light, and it cannot be separated.

DISCLOSURE

Technical Problem

The invention is proposed to solve the described problems. Proposed fluorescent imaging system provides a white light source composed of three narrow-band monochromatic lights which are red, green and blue, further includes the excitation light which is proper to excite the fluorescent material. The invention illuminates the object with white light having a segmented spectrum, not with normal continuous white light. So the reflected light by the light source according to this invention is segmented in spectrum, and the emitted fluorescent light image can be separated from the normal light image as it does not lie in between the wavelength of the light source, which results in the simultaneous acquisition of both images.

SUMMARY

The invention is characterized in that the fluorescent imaging system comprises a mixed light source consisting of white light which includes red, green and blue monochromatic light and a fluorescent excitation light; at least one monochromatic mirror for separating a monochromatic light of particular wavelength from the mixed light source; a fluorescent mirror for separating the light of fluorescent wavelength; natural light imaging devices for photographing the monochromatic light images from the monochromatic mirrors; and a fluorescent imaging device for photographing the fluorescent image from the fluorescent mirror.

In addition, the invention is characterized in that the mixed light source, the normal light imaging device, and the fluorescent imaging device comprises a red-light mirror, green-light mirror, and blue-light mirror that separate red, green, and blue monochromatic light, respectively. It also comprises a fluorescent mirror at the front, back, or in between the red, green, and blue-light mirror where the position of the fluorescent mirror is determined according to the wavelength of fluorescence. However, some of the monochromatic light mirrors may be omitted or integrated together according to the wavelength of fluorescence.

Further, in the fluorescent imaging system according to the particular case of the invention, the monochromatic light mirror is characterized in that it comprises only a red-light mirror for separating red light but may be omitted with a green-light mirror and blue-light mirror if the fluorescent wavelength is longer than the visible light.

Further, in the fluorescent imaging system according to the particular case of the invention, the monochromatic light mirror is characterized in that it comprises only a fluorescent mirror for separating fluorescent light but may be omitted with a red-light mirror, green-light mirror and blue-light mirror if the fluorescent wavelength is shorter than the visible light.

Advantageous Effects

The fluorescent imaging system according to the present invention proficiently delivers an imaging system which simultaneously captures a normal light image and fluorescent image without relying on the complex time-sharing scheme or mechanical device for splitting particular spectrum. It uses reconstructed white light combined with fluorescent excitation light for illumination where the red, green and blue light combined does not cover the whole spectrum, unlike the normal white light whose wavelength range covers all the 380~780 nm range. The fluorescent excitation light may be placed in the vacant spectrum range to separately handles fluorescence without interfering with the normal light image.

Further, the monochromatic lights combined to make white light can be varied as needed, so that variety of fluorescent materials having different characteristic wavelengths may be incorporated into the fluorescent imaging system. In addition, multispectral imaging may be realized because multiple fluorescent materials can be used at the same time although limited by the precision of the optical device.

Further, the concept of the present invention, which can arrange a plurality of dichroic filter and mirrors to acquire multiple fluorescent images simultaneously, is not limited in the field of the laparoscopic device and can apply to other general optical medical devices.

DETAILED DESCRIPTION

A detailed description of the fluorescent imaging system according to the present invention follows.

The fluorescent imaging system according to the present invention comprises mainly of a mixed light source 50 and an imaging system 100. The mixed light source 50 comprises a reconstructed white light with red, green, and blue monochromatic lights combined and a fluorescent excitation light.

Figure 1:
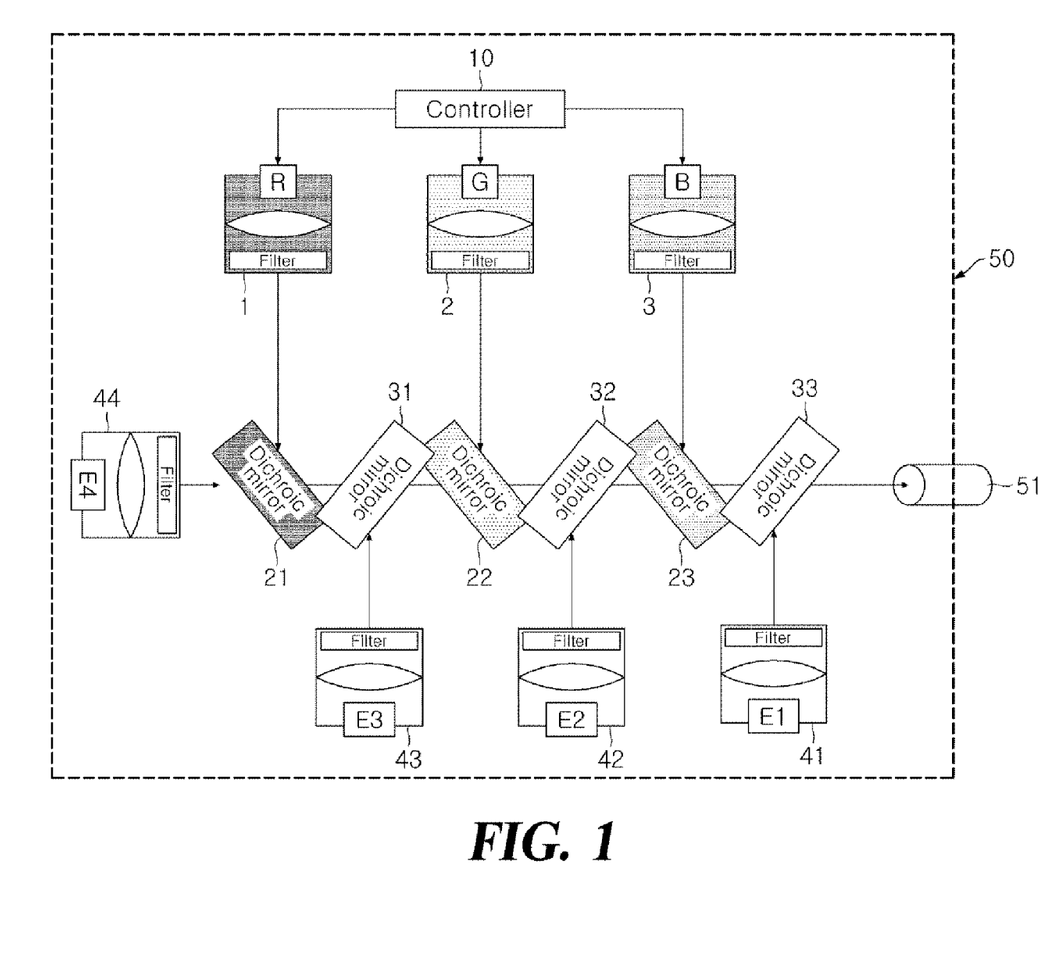
FIG. 1 is a schematic diagram showing a detailed structure of a mixed light source in the fluorescent imaging system according to the present invention.

FIG. 1 is a diagram diagram showing a detailed structure of a mixed light source 50 according to the present invention. A controller 10 controls red-light source 1, green-light source 2, and blue-light source 3 to produce red, green, and blue monochromatic lights. In the present invention, each red, green, and blue light sources 1, 2, 3 having narrow bandwidth may be produced by narrow-band sources such as laser or LED, or by filtering using a narrow band-pass optical filter and a continuous white light source.

Figure 2:
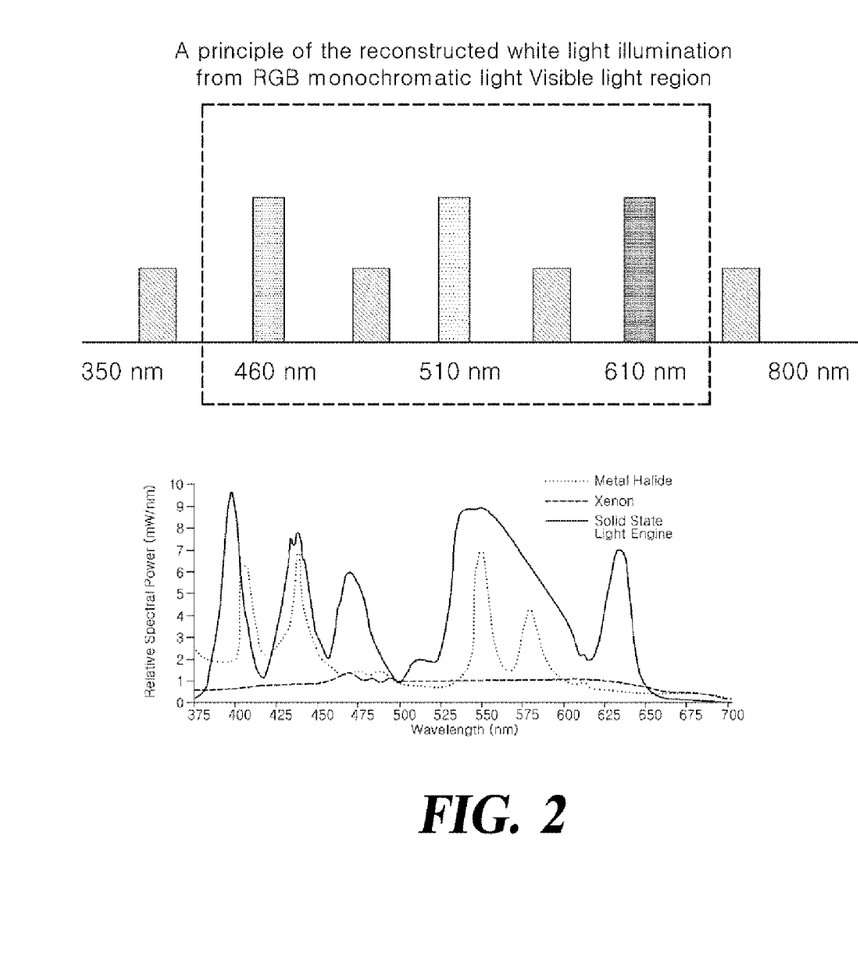
FIG. 2 is a graph showing a principle of the reconstructed white light illumination from RGB monochromatic light in the fluorescent imaging system according to the present invention.
Figure 3:
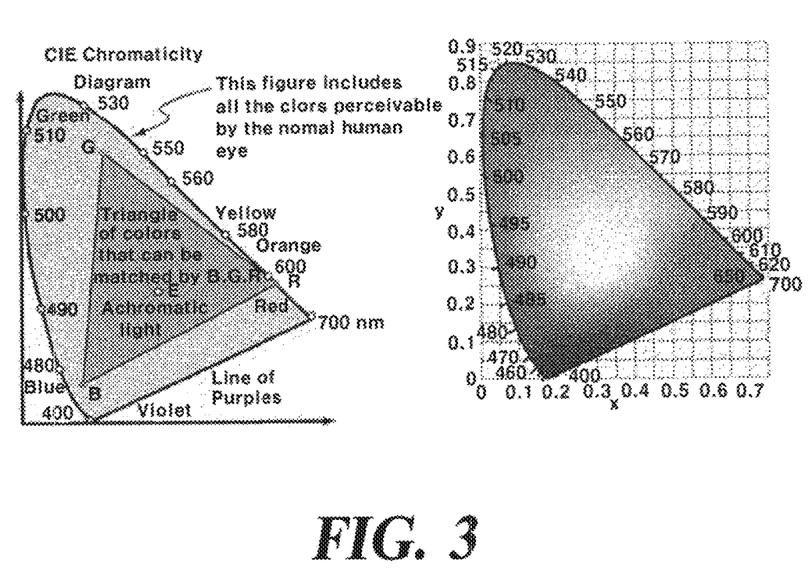
FIG. 3 is a CIE chromaticity diagram illustrating the RGB gamut in the fluorescent imaging system according to the present invention.

In detail, human recognizes the light having a wavelength of 380~780 nm between the UV and IR as shown in FIG. 2. The human eye is known to aware more selectively with red, green, and blue light in this visible range and the brain recognizes various colors in combination of these three colors. In the CIE chromaticity diagram, light coordinated inside the triangle may be obtained in combination of the three colors, red, green, and blue. That is, red, green, and blue light can be properly mixed to make white light even though there may be slight differences or shift in each wavelength range. A reconstructed white light having vacant wavelength regions for fluorescent excitation light and fluorescent emission light may be made using two or more red, green and blue light in combination.

When various monochromatic LEDs are used for source, a variety of color coordinates may be selected to get similar white light because LEDs have narrow bandwidth having the half-width less than 20 nm. White light mixed with general R+G+B LEDs renders color quite correctly, but the white light using LEDs having narrow bandwidth according to the present invention may be hard to render natural white light having high color rendering index (CRI). However, the color rendering quality may be improved by combining more than three monochromatic lights or may be compensated by alternately illuminating with white light.

Red, green, and blue light do not have fixed wavelength range, and proper mixing of them may result in a white color. The mixed light source 50 according to the present invention is a combination of red light ranging 590~750 nm, green light ranging 480~570 nm, and blue light ranging 370~460 nm. It may have a variety of combination as follows.

Combination Example 1—BGR 460 nm+510 nm+610 nm

Combination Example 2—BGR 480 nm+540 nm+700 nm

Additionally, in the present invention, it is desirable to further include an intensity control device for each monochromatic light of red, green, and blue to adjust the color temperature of the mixed light source 50.

The monochromatic lights generated from the red-light source 1, the green-light source 2, and the blue-light source 3 is reflected by each monochromatic light mirror 21, 22, 23, which is a dichroic mirror, then transmitted to the mixing apparatus 51.

In addition, the mixed light source 50 according to the present invention comprises at least one fluorescent excitation light sources 41, 42, 43, 44 that applies to the specific fluorescent material. The fluorescent excitation light sources 41, 42, 43, 44 are respectively equipped with a dedicated optical filter and a source-side fluorescent mirror 31, 32, 33 according to the wavelength of the excitation light.

The mixed light source according to the present invention provides such mixed light source that has a reconstructed white light and a fluorescent excitation light suitable for the fluorescent material in use. Wherein the reconstructed white light is made by mixing red, green, and blue monochromatic light having narrow bandwidth devoid of some spectrum range for the fluorescence excitation and imaging.

Figure 4:
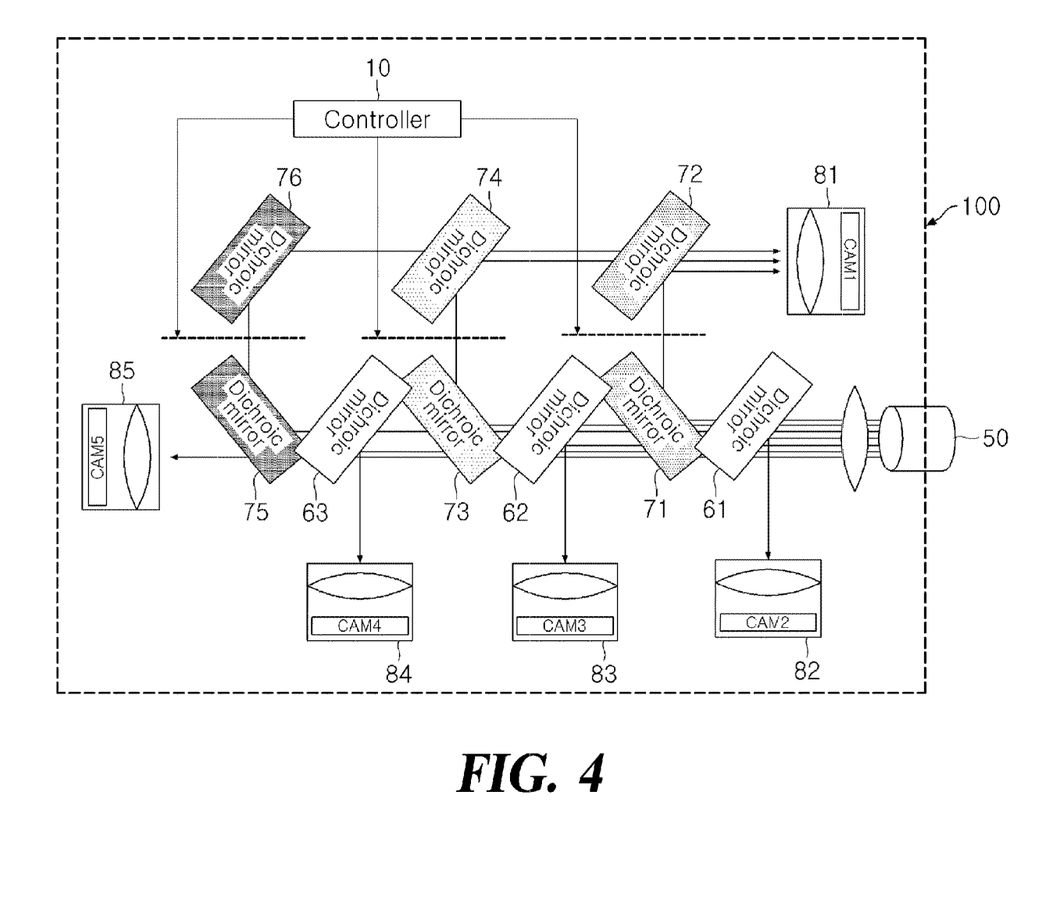
FIG. 4 is a schematic diagram showing a detailed configuration of the imaging device in the fluorescent imaging system according to the present invention.

The imaging system 100 takes a normal light image, fluorescent image, and the mixture of both by separating visible light and fluorescent light reflected from the object illuminated by the mixed light source 50. The imaging system 100 according to the present invention comprises a monochromatic mirror, an imaging-side fluorescent mirror, a normal light imaging device, and a fluorescent imaging device.

The monochromatic mirror separates at least one monochromatic light among the red, green, and blue monochromatic light from the reflected mixed light 50. The monochromatic mirror can be arranged in multiple places according to the location of the natural imaging device.

The monochromatic light mirror in an embodiment of the present invention comprises a pair of blue-light mirrors 71, 72, green-light mirrors 73, 74, and red-light mirrors 75, 76 that reflect the monochromatic light separately according to its corresponding wavelength.

Each monochromatic light mirror according to the present invention may be omitted or integrated according to the wavelength of fluorescence.

The fluorescent mirrors 61, 62, 63 at the imaging system separate the fluorescence light and transmit it to the fluorescent imaging devices. A total of three fluorescent mirrors 61, 62, 63 is comprised in the imaging system in the embodiment of the present invention.

The normal light imaging device 81 takes image by combining each separated monochromatic light from the blue-light mirrors 71, 72, green-light mirrors 73, 74, and red-light mirror 75, 76. The fluorescent imaging devices 82, 83, 84, 85 take images from the emitted fluorescent light from the fluorescent mirrors 61, 62, 63 and may be comprised of a plurality of mirrors depending on the number of fluorescent materials used.

Figure 5:
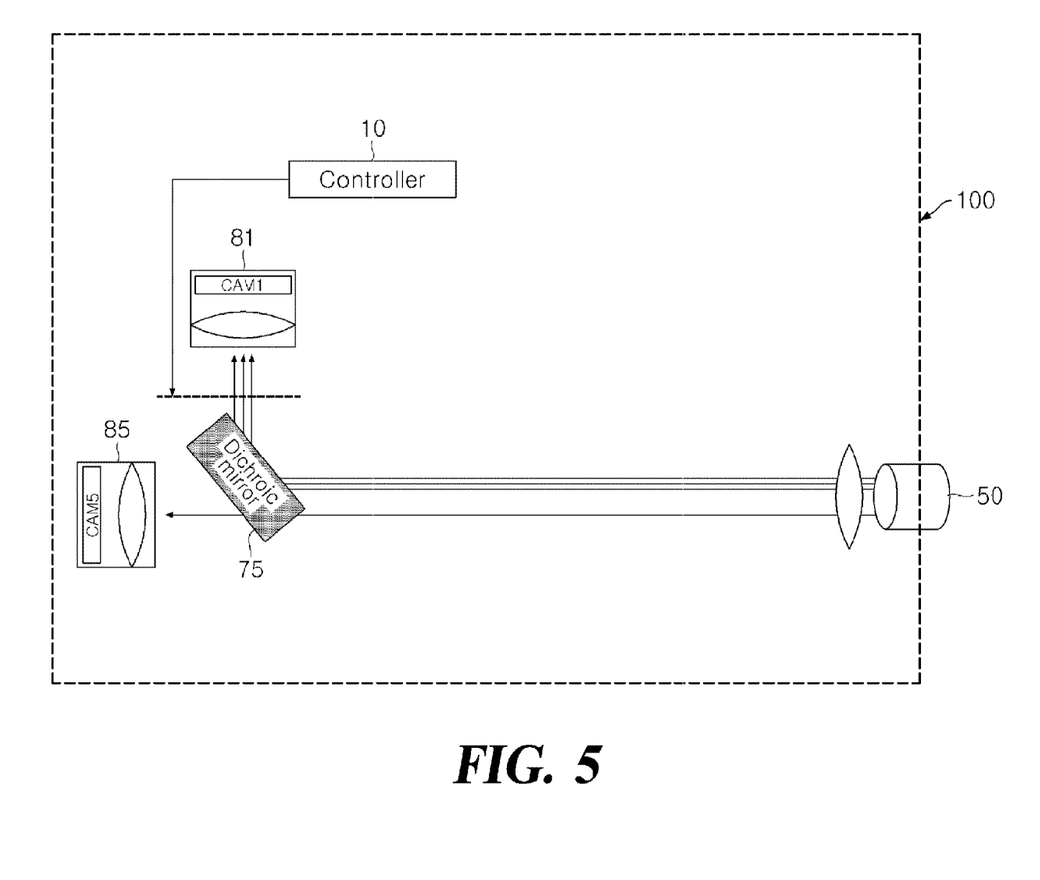
FIG. 5 is a schematic diagram showing a first embodiment of the fluorescent imaging system according to the present invention.

FIG. 5 is a diagram showing a first embodiment of the fluorescent imaging system according to the present invention, and it may correspond in particular to a case of imaging the fluorescence of the indocyanine green and the normal light image.

The indocyanine green has an excitation wavelength of 780 nm and an emission wavelength of 850 nm, longer beyond visible light wavelength. Thus, the imaging device 100 may have only the red-light mirror 75, so the normal light imaging device 81 receives the reflected white light mixed with RGB light, and the fluorescent imaging device 85 receives the transmitted fluorescent light through the red-light mirror 75, both at the same time.

Figure 6:
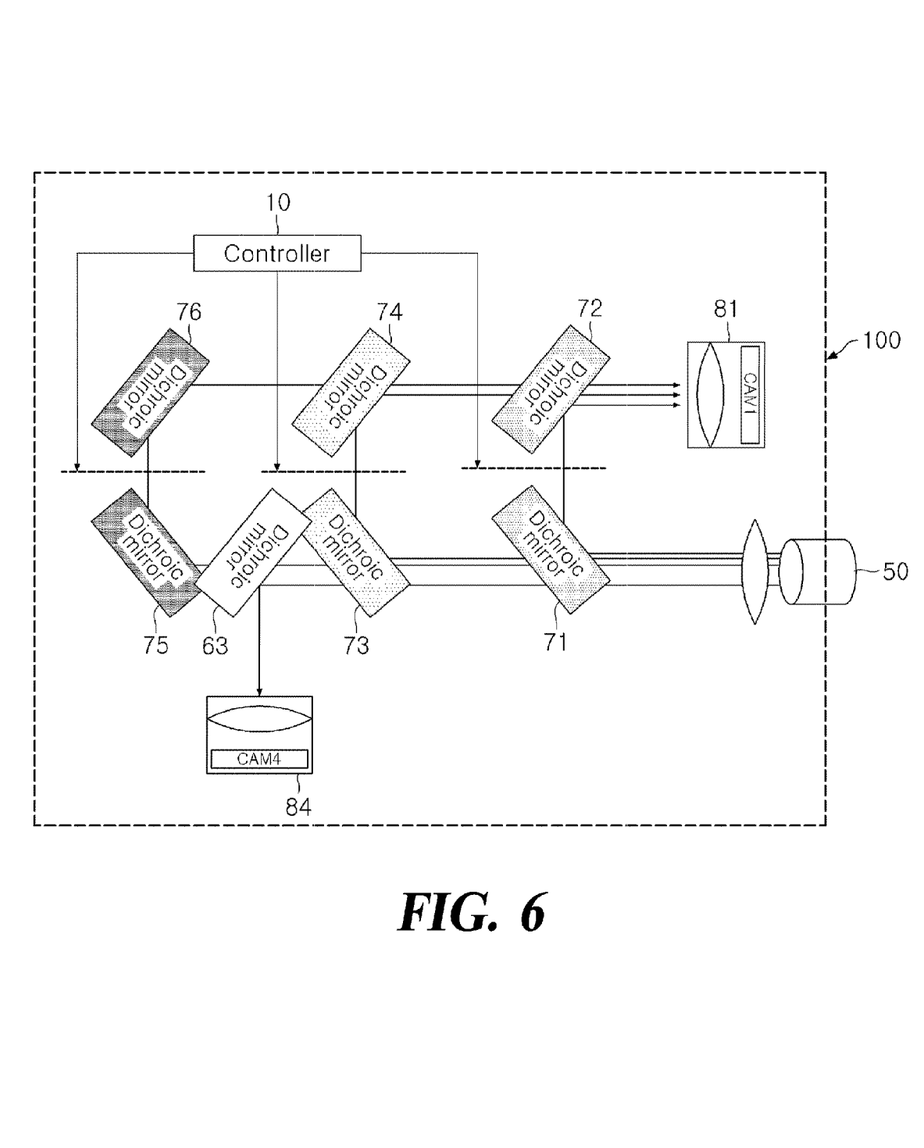
FIG. 6 is a schematic diagram showing a second embodiment of the fluorescent imaging system according to the present invention.

FIG. 6 is a diagram showing a second embodiment of the fluorescent imaging system according to the present invention, and the fluorescent mirror 84 is placed between the red-light mirror 75 and the green-light mirror 73 as the emission wavelength of the fluorescence is in between the red-light and the green-light. This second embodiment may apply to the fluorescent material 5-ALA, to get the fluorescent image and normal light image simultaneously. The 5-ALA has an excitation wavelength of 380~440 nm and an emission wavelength of 635 nm. Thus, the excitation light source is placed in the shorter wavelength range before the blue-light source 3, and the fluorescent mirror 63 is placed between the red-light mirror 75 and the green-light mirror 73.

Figure 7:
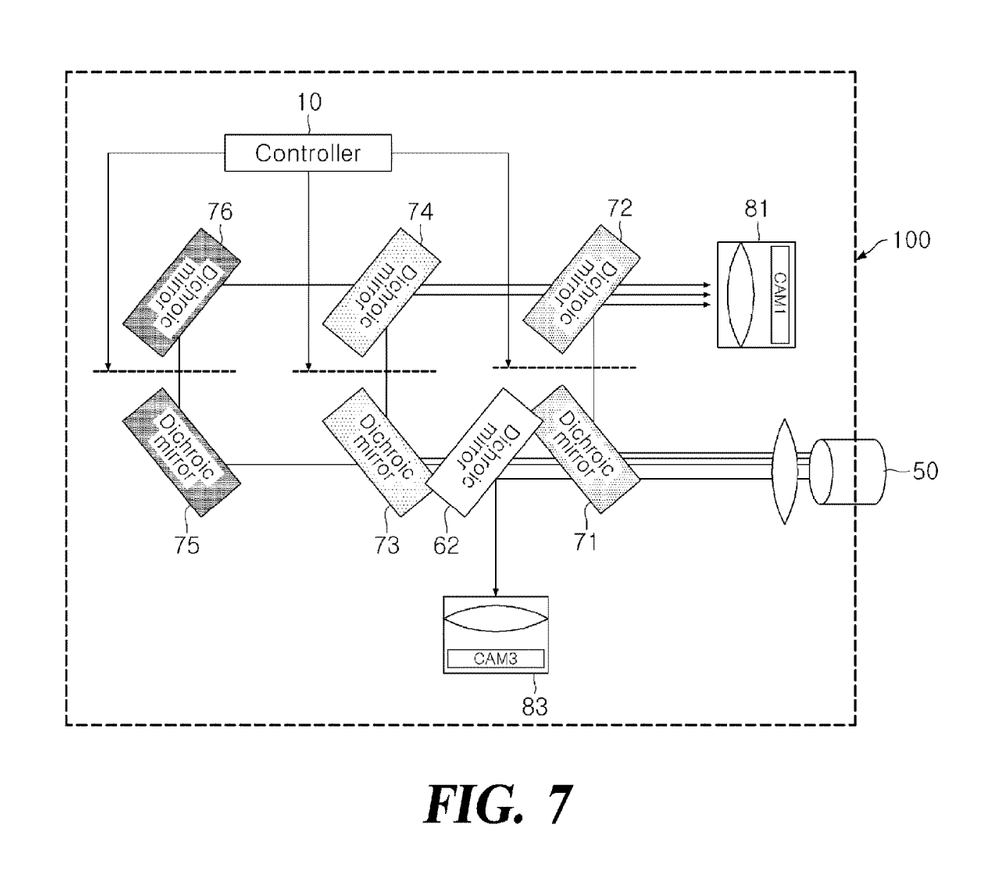
FIG. 7 is a schematic diagram showing a third embodiment of the fluorescent imaging system according to the present invention.

FIG. 7 is a diagram showing a third embodiment of the fluorescent imaging system according to the present invention; it may correspond in particular to a case of imaging the fluorescence of the fluorescein and the normal light image. The fluorescein has an excitation wavelength of 494 nm and an emission wavelength of 521 nm. Thus, the excitation light enters in between the green-light source 2 and the blue-light source 3 in the second embodiment of the white light mixer, and the fluorescent mirror 62 is located between the green-light mirror 73 and the blue-light mirror 71.

Figure 8:
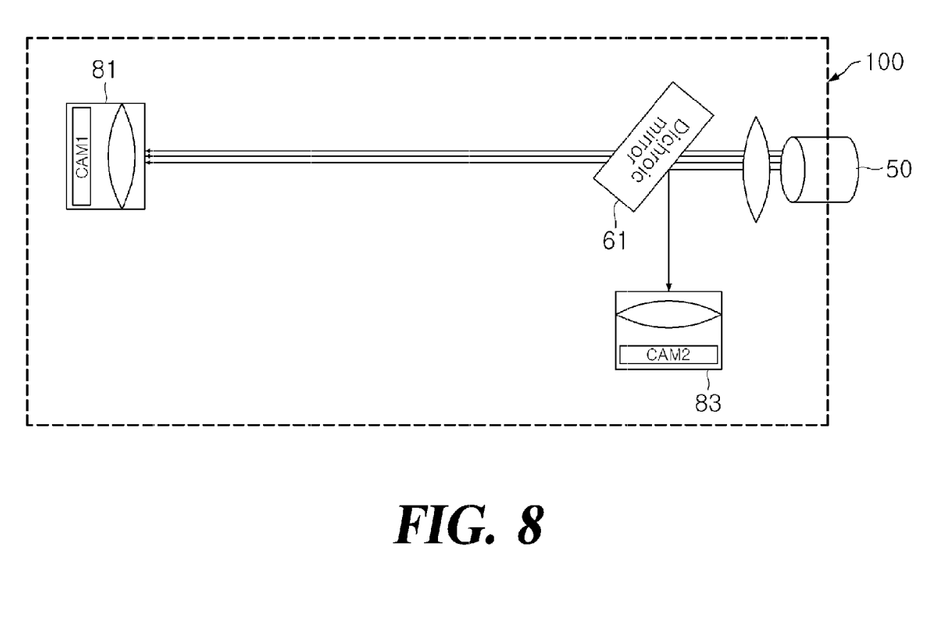
FIG. 8 is a schematic diagram showing a fourth embodiment of the fluorescent imaging system according to the present invention.

FIG. 8 is a diagram showing a fourth embodiment of the fluorescent imaging system according to the present invention, and all monochromatic light mirrors may be omitted except the fluorescent mirror 61 when the emission wavelength of the fluorescence is shorter than that of the blue-light.

Figure 9A:
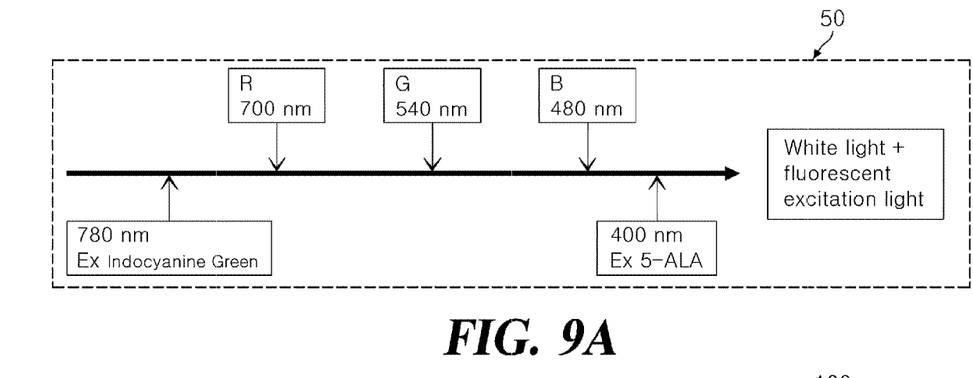
FIG. 9 is a schematic diagram showing the concept of illuminating and acquiring images for the fluorescent imaging system when two fluorescent materials are in use according to the present invention.
Figure 9B:
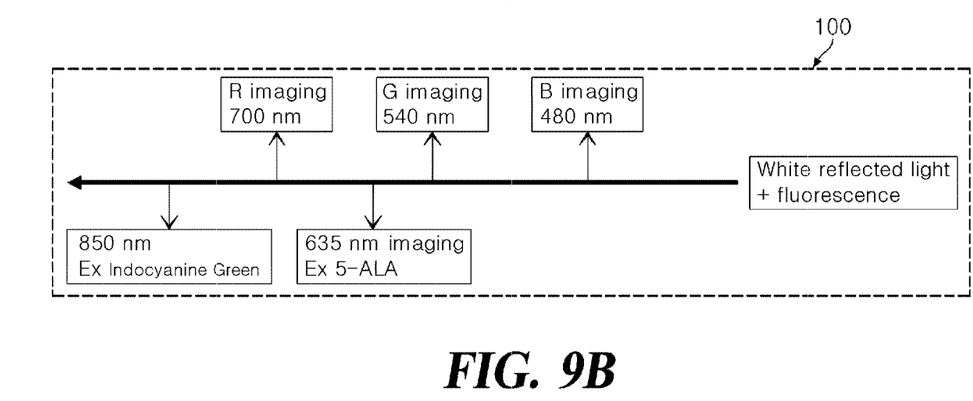

FIG. 9 is a view showing the concept of illuminating and acquiring images for the fluorescent imaging system when two fluorescent materials are in use according to the present invention, and this concept demonstrates simultaneous imaging of the fluorescence of 5-ALA and indocyanine green along with the normal light image.

As described above, the fluorescent imaging system according to the present invention may provide a simultaneous imaging system of the normal light image and the fluorescent image by combining the fluorescent excitation light suitable for the fluorescent material with the reconstructed white light from the monochromatic red, green, and blue light rather than with the continuous white light.

While particular embodiments of the fluorescent imaging system according to the present invention have been shown and described, it will be obvious to those skilled in the art that, based upon the teachings herein, changes and modifications may be made without departing from this invention, and its broader aspects and, therefore, the appended claims are to encompass within their scope all such changes and modifications as are within the true spirit and scope of this invention.

The invention claimed is:

1. A fluorescent imaging system, comprising:
   a mixed light source including
      a monochromatic light source generating a white light from mixing red, green, and blue monochromatic light, and a fluorescent excitation light source for fluorescent imaging, wherein the mixed light source provides a monochromatic light and a fluorescent light; and
   an imaging device separating visible light and fluorescent light from the mixed light and taking a normal light image, a fluorescent image, and mixture of the normal light image and the fluorescent image.

2. The fluorescent imaging system of claim 1, wherein the wavelength of the fluorescence is in a range of the visible light, and
   the imaging device comprises:
      monochromatic mirrors, comprising a red-light mirror, a green-light mirror, and a blue-light mirror that separates red, green, and blue monochromatic light, respectively from the mixed light source;
      a fluorescent mirror that separates the fluorescent light and transmit it to a fluorescent imaging device;
      a normal light imaging device that takes a normal light image by mixing the separated monochromatic lights from the monochromatic mirrors; and
      the fluorescent imaging device that takes a fluorescent image from the fluorescent light separated from the fluorescent mirror.

3. The fluorescent imaging system of claim 1, wherein in case of the wavelength of the fluorescence is longer than the visible light, the imaging device comprises:
a monochromatic mirror, comprising a red-light mirror that separates all the other light of which wavelength are shorter than the red light from the mixed light source;
a normal light imaging device that takes a normal light image from the visible light separated from the red-light mirror; and
a fluorescent imaging device that takes a fluorescent image from the fluorescent light separated from the red-light mirror.

4. The fluorescent imaging system of claim 1, wherein in case of the wavelength of the fluorescence is shorter than the blue light, the imaging device comprises:
a fluorescent mirror, separating the fluorescent light of which wavelength is shorter than the blue light and the white light from the mixed light source, and transmitting the separated fluorescent light to a fluorescent imaging device;
a normal light imaging device that takes a normal light image from the visible light separated from the fluorescent mirror; and
the fluorescent imaging device that takes a fluorescent image from the fluorescent light separated from the fluorescent mirror.

5. The fluorescent imaging system of claim 1, wherein the mixed light source is generated by mixing the red, green, and blue light having wavelengths of about 590~750, 480~570, and 370~460 nm, respectively.

6. The fluorescent imaging system of claim 1, wherein the fluorescence excitation light source applies to at least one fluorescent material among indocyanine green, fluorescein, and 5-ALA.

7. The fluorescent imaging system of claim 1, further comprising intensity control devices for adjusting the color temperature when mixing the red, green, and blue monochromatic light to generate the white light.

\* \* \* \* \*